US006361960B1

(12) United States Patent
Pliszka et al.

(10) Patent No.: US 6,361,960 B1
(45) Date of Patent: Mar. 26, 2002

(54) METHOD AND TEST KIT FOR MEASURING CONCENTRATION OF A CLEANING AGENT IN A WASH LIQUOR

(75) Inventors: Matthew E. Pliszka, Whitefish Bay; Leza Luchetta, Madison, both of WI (US)

(73) Assignee: Environmentally Sensitive Solutions, Inc., Shorewood, WI (US)

( * ) Notice: Subject to any disclaimer, the term of this patent is extended or adjusted under 35 U.S.C. 154(b) by 0 days.

(21) Appl. No.: 09/436,619

(22) Filed: Nov. 9, 1999

(51) Int. Cl.[7] .......................... C12Q 1/54; C12Q 1/26; C12Q 1/28; C12Q 1/00; G01N 21/00
(52) U.S. Cl. ................. 435/14; 435/4; 435/25; 435/28; 436/164
(58) Field of Search ................ 435/14, 4, 25, 435/28; 436/64

(56) References Cited

U.S. PATENT DOCUMENTS

| | | | |
|---|---|---|---|
| 2,408,900 A | | 10/1946 | Alston et al. |
| 4,340,669 A | * | 7/1982 | Bauer |
| 4,867,193 A | | 9/1989 | Hayashi et al. |
| 5,041,386 A | | 8/1991 | Pierce et al. |
| 5,077,476 A | | 12/1991 | Rosenthal |
| 5,086,229 A | | 2/1992 | Rosenthal et al. |
| 5,266,493 A | | 11/1993 | Young |
| 5,304,468 A | | 4/1994 | Phillips et al. |
| 5,498,546 A | * | 3/1996 | Kuhlmann et al. |

OTHER PUBLICATIONS

Bayer Corporation (Diagnostics Division), "Diastix® Reagent Strips/Test Information and Procedure, A Visual Urine Test for Glucose" (Brochure AN0456B, 1985).

Environmentally Sensitive Solutions, Inc., "Shift to Neutral," *Parts Cleaning* magazine (Apr. 1998).

Environmentally Sensitive Solutions, Inc. "ESS, The Neutral Solution®, We've solved the problems of alkaline degreasers". (Information Sheet).

Environmentally Sensitive Solutions, Inc., Internet pages from website www.neturalsolution.com. ("We've solved the problems of alkaline degreasers."; "What are neutral cleaners?").

* cited by examiner

*Primary Examiner*—Ralph Gitomer
*Assistant Examiner*—Mahreen Chaudhry
(74) *Attorney, Agent, or Firm*—Charles L. Leeck; Godfrey & Kahn, S.C.

(57) ABSTRACT

A method of determining the concentration of a surfactant-based neutral cleaner in a wash liquor, a hand-held apparatus, and a test kit for carrying out the method are provided. According to the method, a cleaner composed of the cleaning agent, an amount of a reducing sugar that is proportional to the cleaning agent, and a sugar preserving agent, is added to a wash solution. A sample of the resulting wash liquor is applied to an enzyme system that reacts with the reducing sugar to form a colored end product. After a suitable time interval, the color of the reaction product can be photometrically measured to provide a color intensity value that is correlated to the amount of reducing sugar in the wash liquor, which, in turn, is correlated to the amount of cleaning agent in the wash liquor. The portable apparatus can be packaged with associated test supplies and reagents in a test kit.

17 Claims, 1 Drawing Sheet

METHOD AND TEST KIT FOR MEASURING CONCENTRATION OF A CLEANING AGENT IN A WASH LIQUOR

FIELD OF THE INVENTION

The present invention relates to a method, apparatus, and test kit for measuring and monitoring the concentration of a cleaning agent in a liquid, more particularly a surfactant-based neutral cleaning agent in a wash liquor.

BACKGROUND OF THE INVENTION

In commercial cleaning of process oils and grease from metal parts, tools and other metal surfaces commonly found in maintenance departments, auto service shops, and metal processing industries, there has been a shift over the years from solvent washer systems to aqueous-based cleaners. Of those cleaners, alkaline cleaning products have become widely used.

Alkaline cleaners chemically react with most oils by saponification, whereby the oil is chemically changed to a partially soluble soap, which cannot be easily separated from the wash water. A drawback of alkaline cleaning products is that they cannot be discharged to a sewer system due to heavy metals and chelators in the solution. In addition, the high alkaline pH between 8.0 and 12.0 further complicates the wastewater treatment process. Alkalines also become consumed during the saponification process, which necessitates constantly adding more cleaner to replace what has been consumed.

The advent of surfactant-based neutral cleaners (SBNs) has provided a new option for aqueous degreasers for cleaning hard surfaces. SBNs have a neutral use pH of between 7.0 and 8.0, and are all organic, provide superior rinsability, greater foam control, mildness to the skin, longer shelf life, eliminate many wastewater problems and washer corrosion, do not leave the characteristic white film of alkaline products, and provide an "all-in-one" product that is safe on all kinds of metal surfaces. In the area of wastewater treatment, SBNs reduce the need for pH adjustment prior to discharge, thus eliminating the costs associated with acid neutralization. Because of the neutral pH, bioremediation becomes a viable wastewater treatment option. Unlike alkaline degreasers, neutral cleaners clean by a mechanism of emulsification whereby they surround oil molecules with a micelle formed by agitation and impingement of the oily surface. The micelles prevent the oil from re-attaching to the metal surface and, when the agitation stops, release the oil to the surface where it can be removed by traditional recovery methods. Unlike alkalines, once the excess oil is recovered, the neutral soap is available for cleaning again, which extends the life of the bath solution.

In a wash process, it is desirable to monitor the concentration of the cleanser in the wash solution throughout the operation in order to maintain the cleanser at a consistent level. Current methods for testing the concentration of an alkaline detergent in a wash liquor include fluorescence, conductivity and, most commonly for metal cleaners, acid-base titration based on a phenolphthalein indicator end point. A drawback, of these methods is that they give an inaccurate analysis due to soil loading. In addition, conductivity must be empirically determined for each detergent.

U.S. Pat. No. 5,4998,546 (Kuhlmann et al.) discloses another method for determining the concentration of an alkaline detergent in an industrial laundry wash liquor, by adding a reducing sugar to the wash liquor in an amount proportional to the detergent composition, chemically reacting the sugar with an aromatic hydrazine compound, and photometrically measuring the color. However, the test procedure is time consuming, and requires multiple reagent solutions, heating and temperature control for accurate results, and an extended reaction time to induce a color change. In addition, a PC is needed as an instrument-operator interface, relatively complicated instrumentation is used, the set-up is expensive, and frequent-calibration of instruments is required.

Currently used methods for determining the concentration of SBNs in a washer bath are acid-base titration and EDTA titration, which involve adding an indicator to a small volume of the wash solution and measuring the amount of titrant required to induce a color change. Problems with these methods include interference caused by lubricants, oils, rust inhibitors and additives in the washer bath, inconsistent results from bath to bath, the need for multiple chemical reagents, difficulty in distinguishing a color change in a dirty or murky bath, and the need to conduct multiple steps for the analysis. In addition, the use of EDTA in the cleaner formulation as a metal chelator causes wastewater concerns due to increased heavy metal discharge. To date, there are no procedures for readily and accurately testing the concentration of a surfactant-based neutral cleaner (SBN) in a wash liquor.

Therefore, an object of the invention is to provide a method for readily and accurately determining the concentration of surfactant-based neutral cleaners (SBNs) in a wash liquor that overcomes the disadvantages of current testing methods.

SUMMARY OF THE INVENTION

These and other objects are achieved by the present invention, which is directed to a method of determining the concentration of a cleaning agent in a wash liquor, particularly a surfactant-based neutral cleaning agent, an apparatus for carrying out the method, and a test kit containing the apparatus and associated test items and reagents.

According to the method, a wash liquor is combined with a solution containing a mixture of the cleaning agent, an amount of a reducing sugar that is proportional to the cleaning agent, and a sugar preserving agent. The solution of the cleaning agent and reducing sugar preferably contains about 0.5–3.0% reducing sugar, more preferably about 2%. To test for the concentration of the cleaning agent in the wash liquor, an aliquot or portion of the wash liquor is removed and reacted with an enzyme composition to induce an enzymatic reaction with the reducing sugar and produce a colored reaction product. The enzyme composition is typically composed of an oxidase enzyme, peroxidase, and an indicating agent that will produce a colored product when the sugar is reacted with the enzyme composition. In the use of glucose as the reducing sugar, glucose oxidase is a preferred component of the enzyme composition.

The intensity of the color of the enzyme/sugar reaction product can be measured photometrically using light at an appropriate wavelength. The color intensity value is then correlated with the concentration of the reducing sugar, which, in turn, is correlated to the concentration of the cleaning agent in the wash liquor. An approximate concentration of the reducing sugar in the wash liquor can be determined by comparing the color of the reaction product to a color chart.

The method is useful for monitoring the concentration of the cleaning agent in a wash liquor over time by occasionally or at set intervals, removing a portion of the wash liquor, reacting it with the enzyme composition, and measuring and correlating the color intensity of the reaction product to the concentration of the cleaning agent in the wash liquor.

In a preferred method, an aliquot of the wash liquor is deposited onto an enzyme composition that is immobilized on a solid support such as a plastic test strip. The intensity of the color of the reaction product can be determined photometrically by transmitting a beam of light at the desired wavelength onto the solid support and to a light detector that receives the light reflected from the reaction product.

In implementing the method, it is desirable to use a portable, hand-held apparatus that is designed to measure the concentration of the reducing sugar and correlate that amount to the concentration of the cleaning agent in the wash liquor. Such a device includes a member for removably receiving the solid support (test strip), a light source for applying a beam of light at the desired wavelength onto the solid support, and a member for detecting the light reflected from the reaction product on the solid support. The detecting member is operable to produce an output signal that is proportional to the light that is detected. The device further includes a microprocessor that receives and processes the output signal, and is programmed to correlate the output signal to the concentration of the reducing sugar and, preferably, to process and correlate the concentration of the reducing sugar to the concentration of the cleaning agent in the wash liquor. In use of the apparatus, a test strip with the enzyme composition immobilized on it is inserted into the receiving slot, and a drop of the wash liquor is deposited onto the enzyme composition. The enzymatic reaction typically proceeds for about 30–60 seconds, whereupon the apparatus photometrically measures the color intensity of the reaction product and processes the data to arrive at the concentration of the reducing sugar, and preferably the cleaning agent, in the wash liquor. The value is then displayed and/or printed out for the user.

A test kit is provided that contains the portable, hand-held apparatus packaged together with other items and reagents used in the test method. Such items can include test strips with the enzyme system immobilized thereon, instructions for using the apparatus and other testing items according to the method of the invention, a calibration standard curve of the sugar concentration versus the cleaning agent concentration, and, optionally, a container or package of the cleaning agent, reducing sugar and sugar preservative.

Advantageously, the present method provides a quick, easy, accurate, and reliable assay for testing the concentration of a surfactant-based neutral cleaner in a wash liquor. The assay employs an indicating agent, i.e., the reducing sugar, which is biodegradable and non-toxic, eliminates the need for hazardous chemical reagents, and will not affect the wash process or cleanliness of the part or item being cleaned. The present method and apparatus also decrease the time required for testing the amount of cleaner in a wash liquor, and requires the use of relatively inexpensive instrumentation.

BRIEF DESCRIPTION OF THE DRAWINGS

Throughout the following views, reference numerals will be used on the drawings, and the same reference numerals will be used throughout the several views and in the description to indicate same or like parts of the invention.

DETAILED DESCRIPTION

Figure 1:
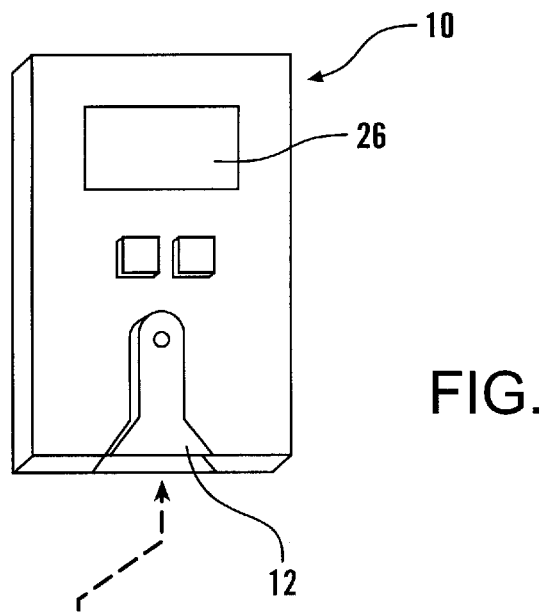
FIG. 1 is a perspective view of an apparatus for use in determining the concentration of a cleaning agent in a wash liquor according to the present invention.

The invention provides a rapid and simple assay for reliably determining the concentration of a surfactant-based neutral cleaner in a wash liquor, and an apparatus and test kit for use in the method. The method can also be used to measure the concentration of other process chemicals such as those classified as aqueous-based lubricants, coolants, rust inhibitors, derusting agents, defoamers, among others.

The term "wash liquor" as used herein is a water-based solution that includes a cleaning agent, typically at a use concentration of about 1–10%. A typical wash liquor made with a surfactant-based neutral cleaner is a water-based solution composed of surfactants, propylene glycol ethers, rust inhibitor and preservatives.

According to the invention, a reducing sugar is combined with the cleaning agent, and the mixture is then added to the wash liquor. The wash liquor containing the cleaning agent has a pH of about 6.0–8.5. Glucose is the preferred reducing sugar, although other reducing sugars such as fructose, maltose, galactose, and lactose can also be used. Preferably the reducing sugar/cleaning agent mixture is formulated to include about 0.5–3.0% by weight sugar (or about 5–30 gm/l), preferably about 1–2% by weight, most preferably about 2% by weight. By combining the reducing sugar with the cleaning agent and adding the mixture to the wash liquor, rather than directly adding the sugar alone to the wash liquor, it is assured that the amount of reducing sugar that is present in the wash liquor is proportional to the concentration of the cleaning agent. This provides for a reliable indirect measurement of the cleaning agent in the wash liquor.

The reducing sugar and cleaning agent solution further includes a preservative such as sodium benzoate, to inhibit microbial degradation of the sugar. The inclusion of a sugar-preserving agent helps maintain a constant amount of sugar in the concentrated cleaning agent/reducing sugar solution and in the wash liquor by preventing degradation of the sugar. Preferably, the cleaning agent/reducing sugar solution includes about 0.4–6% sodium benzoate or other preserving agent, preferably about 1–3%, preferably about 2%.

A sample or aliquot of the wash liquor is removed and reacted with an enzyme composition at a temperature and for a time effective to induce an enzymatic reaction with the reducing sugar resulting in a colored reaction product. The assay does not require close temperature control for accurate results and can be run over a wide temperature range (about 70–160° F.). The color intensity of the reaction product is then measured and correlated to the concentration of the reducing sugar and to the cleaning agent in the wash liquor.

In one embodiment of the invention, an aliquot of the wash liquor containing the reducing sugar is placed onto a solid support on which an enzyme composition is immobilized. The enzyme composition typically includes an oxidase enzyme, peroxidase, and an indicator compound that undergoes a reaction with the peroxidase to produce a colored, light-absorbing product. Where the reducing sugar is glucose, the enzyme composition can be composed of glucose oxidase, peroxidase, and an indicator compound such as O-dianisidine, O-tolidine, benzidine, an MBTH-DMAB (3-methyl-2-benzothiazolinone hydrazone hydrochloride and 3-dimethylaminobenzoic acid) dye couple, an AAP-CTA (4-aminoantipyrene and chromotropic acid) dye couple, O-toluidine, 2,2'-azinodi-(3-ethylbenzthiazoline sulphonic acid-6), 3-methyl-2-benzothiazolinone hydrazone plus N,N-dimethylaniline, phenyl plus aminophenazone, sulfonated 2,4-dichlorophenol plus 4-aminophenazone, 2-methoxy-4-allyl phenol, and 4-aminoantipyrene-dimethylaniline, among others. Such glucose test strips are commercially available, for example, under the tradename One Touch® test strips, from Lifescan, Inc., Mountain View, Calif., and are composed of about 14 IU/cm$^2$ glucose oxidase, about 11 IU/cm$^2$ peroxidase, about 0.06 mg 3-methyl-2-benzothiazolinone hydrazone hydrochloride (MBTH), and about 0.12 mg 3-dimethylaminobenzoic acid (DMAB).

When the sample of the wash liquor containing the reducing sugar, is brought into contact with the enzyme composition, preferably at about room temperature, the enzyme reagent chemically reacts with the reducing sugar to produce a colored reaction product and a change in reflectance that indicates the concentration of the reducing sugar in the sample. For example, with glucose as the reducing sugar, the glucose oxidase enzyme oxidizes the glucose to gluconic acid forming hydrogen peroxide as a reaction product, and the peroxidase enzyme catalyzes an oxidative coupling of the hydrogen peroxide with the indicator compound which undergoes a color reaction to give a color proportional in intensity to the glucose level in the sample. The liquid sample remains in contact with the enzyme composition for an effective reaction time for color development, typically about 30–60 seconds.

Although not preferred due to low precision and accuracy compared to the photometric method, an approximate concentration of the reducing sugar can also be determined by visually comparing the color of the enzyme/sugar reaction product to a standard color chart calibrated to various concentrations of the reducing sugar, and matching the color of the sample with the corresponding color zone on the chart, which represents a range of values. Paper and/or plastic test strips containing the enzyme composition are useful in a visual comparison of the color of the reaction product. Such test strips are commercially available and include, for example, Diastix® reagent strips from Bayer Corporation, Elkhart, Ind. (2.2% w/w glucose oxidase, 1.0% w/w horseradish peroxidase, 8.1% w/w potassium iodide, 69.8% w/w buffer, 18.9% w/w non-reactive ingredients).

Preferably, the color intensity of the reaction product is determined by means of an instrument such as a diffuse reflectance spectrophotometer with associated software that reads reflectance, and calculates and correlates the color intensity to the level of the reducing sugar in the liquid sample. The device can provide a readout of the sugar concentration, which can then be correlated to the concentration of the cleaning agent in the wash liquor according to a standard curve or calibration graph of sugar concentration vs % cleaner in the wash liquor. In a preferred embodiment, the device is further programmed to correlate the concentration of the reducing sugar to the concentration of the cleaning agent in the wash liquor based on the proportional amount of the reducing sugar in the sugar/cleaning agent mixture that was added to the wash, or using a calibration curve programmed into the device.

In a preferred method, a portable, hand-held apparatus is used to photometrically measure the intensity of the enzyme color reaction product on a solid support such as a transparent test strip. An example of such a device is described, for example, in U.S. Pat. No. 5,304,468, and commercially available as the One Touch® blood glucose monitoring System from Lifescan, Inc., Mountain View, Calif. Such a commercial device will provide a read-out of the concentration of the reducing sugar in the test sample, which can then be correlated to the concentration of the cleaning agent in the wash liquor, based on an established standard curve.

Figure 2:
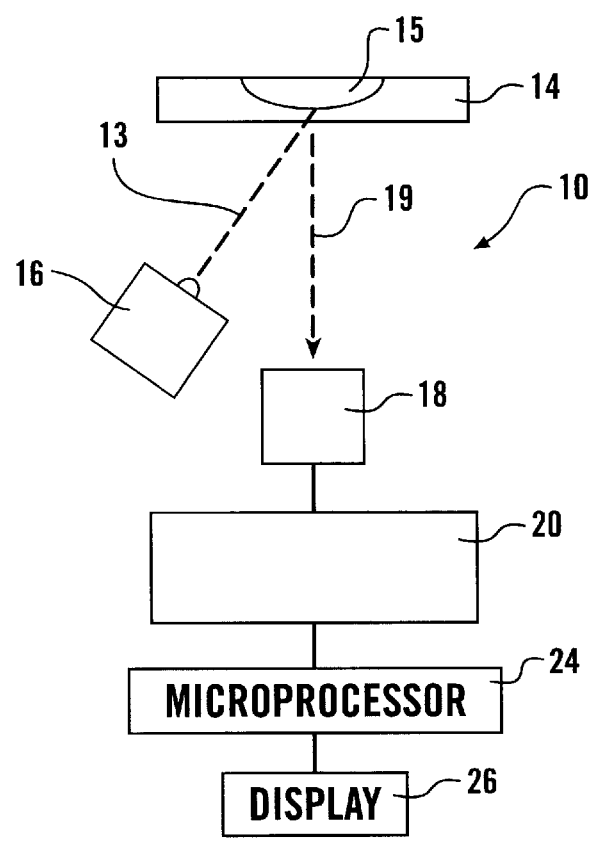
FIG. 2 is a schematic of the apparatus of FIG. 1.

As depicted in FIGS. 1 and 2, such an apparatus 10 includes a member 12 for removably receiving a test strip (solid support) therein, a light source 16 such as a high intensity LED for applying a beam of light 13 to the test strip 14 at a suitable wavelength according to the absorption of the colored reaction product, a member 18 for detecting the light 19 reflected from the test strip 14 such as a phototransistor that produces an output signal (current) proportional to the light it receives. Test strip 14 has an enzyme system 15 immobilized thereon, and receives an aliquot of wash liquor for reaction with the enzymes to produce the enzymatic reaction product. An electronics component 20 such as a linear integrated circuit, converts the current to a voltage and to a digital signal to be received by a microprocessor 24. The microprocessor 24 is composed of components to store and process the data from the reflectance measurements to arrive at the concentration of the reducing sugar, and output that data to a digital display 26. The display 26 is preferably a LCD or LED display.

According to the invention, for a direct readout of the concentration of the cleaning agent in the wash liquor, the microprocessor 24 can be further programmed to correlate the concentration of the reducing sugar to the concentration of the cleaning agent in the wash liquor according to a set of predetermined values based on the proportional amounts of the reducing sugar and cleaning agent in the sugar/cleaning agent mixture that was added to the wash liquor.

In the use of such a portable device 10 to monitor the amount of a cleaning agent in a wash liquor accordingly to the present method, a test strip 14, preferably a mylar or other plastic strip that is light transmissive, having the enzyme composition 15 immobilized thereon is inserted into the slot in the receiving member 12 for the test strip 14 (solid support) and aligned with the light source 16. An aliquot of the wash liquor, preferably a drop or about 0.05 ml, is placed on the test strip 14 and allowed to react with the enzyme reagent 15 to form an immobilized colored reaction product. The apparatus 10 is then activated to photometrically measure the color intensity of the reaction product at an appropriately set wavelength. The data processor 24 then correlates intensity of the color of the reaction product to the concentration of the reducing sugar in the wash liquor, which, being proportional to the amount of the cleaning agent, is then correlated to the concentration of the cleaning agent in the wash liquor.

The portable, hand-held apparatus 10 can be packaged in a test kit or article of manufacture, together with one or more of the following items: a container of the cleaning agent combined with a proportional amount of the reducing sugar, a package of test strips with the enzyme composition immobilized thereon, instructions for using the foregoing items for measuring the concentration of the cleaning agent added to a wash bath or other liquid, a calibration standard curve of the concentration of the reducing sugar to the % cleaner in the wash liquor, Material Safety Data Sheet (MSDS), and pipettes and other like tools for use in the assay. In a preferred form, the cleaning agent/sugar mixture is composed of a surfactant-based neutral cleaner combined with about 2% glucose, and the enzyme composition is composed of glucose oxidase, peroxidase, and an indicator component.

The invention has been described by reference to detailed examples and methodologies. These examples are not meant to limit the scope of the invention. Variations within the concepts of the invention are apparent to those skilled in the art. The disclosures of the cited references throughout the application are incorporated by reference herein.

What is claimed is:

1. A method of measuring concentration of a surfactant-based neutral cleaning agent in a wash liquor, comprising:
   a) providing a wash liquor comprising a mixture of the surfactant-based neutral cleaning agent, an amount of a reducing sugar proportional to the cleaning agent, and a sugar preserving agent, said sugar preserving agent being added to the mixture to inhibit microbial degradation of the reducing sugar;
   b) reacting a portion of the wash liquor with an enzyme composition to induce an enzymatic reaction with the reducing sugar to produce a colored reaction product;
   c) photometrically measuring color intensity of the reaction product; and
   d) correlating the color intensity of the reaction product to the concentration of the surfactant-based neutral cleaning agent in the wash liquor.

2. The method of claim 1, wherein step b) comprises contacting the wash liquor with a solid support having the enzyme composition immobilized thereon, and step c) comprises transmitting a light onto the solid support and to a member operable to receive light reflected from the reaction product.

3. The method of claim 1, wherein the cleaning agent/reducing sugar mixture of step a) comprises about 0.5–3.0% reducing sugar.

4. The method of claim 1, wherein the cleaning agent/reducing sugar mixture of step a) comprises about 2% reducing sugar.

5. The method of claim 1, wherein the enzyme composition comprises an oxidase enzyme, peroxidase, and an indicating agent capable of producing the colored reaction product.

6. The method of claim 5, wherein the reducing sugar is glucose, and the oxidase enzyme is glucose oxidase.

7. The method of claim 6, wherein the indicating agent is selected from the group consisting of O-dianisidine, O-tolidine, benzidine, a (3-methyl-2-benzothiazolinone hydrazone hydrochloride and 3-dimethylaminobenzoic acid) dye couple, a (4-aminoantipyrene and chromotropic acid) dye couple, O-toluidine, 2,2'-azinodi-(3-ethylbenzthiazoline sulphonic acid-6), 3-methyl-2-benzothiazolinone hydrazone plus N,N-dimethylaniline, phenyl plus aminophenazone, sulfonated 2,4-dichlorophenol plus 4-aminophenazone, 2-methoxy-4-allyl phenol, and 4-aminoantipyrene-dimethylaniline.

8. The method of claim 1, wherein step d) comprises correlating the color intensity of the reaction product to the concentration of the reducing sugar in the wash liquor, and correlating the concentration of the reducing sugar to the concentration of the surfactant-based neutral cleaning agent in the wash liquor.

9. The method of claim 1, further comprising monitoring the concentration of the cleaning agent in the wash liquor over time by removing and reacting a portion of the wash liquor with the enzyme composition at intervals over time, and measuring and correlating the color intensity of the respective reaction product to the concentration of the cleaning agent in the wash liquor.

10. The method of claim 1, wherein the wash liquor containing the cleaning agent has a pH of about 6.0–8.5.

11. A method of measuring concentration of a cleaning agent in a wash liquor, comprising:
    a) providing a wash liquor comprising a mixture of the cleaning agent, an amount of a reducing sugar proportional to the cleaning agent, and a sugar preserving agent, said sugar preserving agent being added to the mixture to inhibit microbial degradation of the reducing sugar;
    b) reacting a portion of the wash liquor with an enzyme composition to induce an enzymatic reaction with the reducing sugar to produce a colored reaction product;
    c) measuring color intensity of the reaction product; and
    d) correlating the color intensity of the reaction product to the concentration of the cleaning agent in the wash liquor.

12. The method of claim 11, wherein the cleaning agent is a surfactant-based neutral cleaner.

13. The method of claim 11, wherein the cleaning agent is selected from the group consisting of a water-based lubricant, coolant, rust inhibitor, defoamer, and derusting agent.

14. The method of claim 11, wherein the reducing sugar is glucose, and the enzyme composition comprises glucose oxidase, peroxidase, and an indicating agent.

15. The method of claim 11, wherein step b) comprises contacting the wash liquor with the enzyme composition immobilized on a solid support in the form of a test strip.

16. The method of claim 15, wherein step c) comprises photometrically measuring the color of the reaction product by transmitting a light onto the reaction product on the test strip and to a member operable to receive light reflected from the reaction product.

17. The method of claim 11, wherein step c) comprises visually comparing the color of the reaction product to a standard color chart calibrated to various concentrations of the reducing sugar reacted with the enzyme composition.

* * * * *